United States Patent [19]
Klicek

[11] Patent Number: 5,221,281
[45] Date of Patent: Jun. 22, 1993

[54] ELECTROSURGICAL TUBULAR TROCAR

[75] Inventor: Michael S. Klicek, Boulder, Colo.

[73] Assignee: Valleylab Inc., Boulder, Colo.

[21] Appl. No.: 906,591

[22] Filed: Jun. 30, 1992

[51] Int. Cl.⁵ .............................................. A61B 17/35
[52] U.S. Cl. ...................... 606/45; 606/184; 606/185; 606/39; 604/164
[58] Field of Search ................ 606/167, 184, 185, 32, 606/37, 39, 45, 48, 28, 29; 604/164

[56] References Cited
U.S. PATENT DOCUMENTS

| | | | |
|---|---|---|---|
| 4,682,596 | 7/1987 | Bales et al. | 606/45 X |
| 4,721,506 | 1/1988 | Teues | 604/164 X |
| 5,009,643 | 4/1991 | Reich et al. | 606/185 X |
| 5,088,997 | 2/1992 | Delahuerga et al. | 606/45 X |
| 5,183,464 | 2/1993 | Dubrul et al. | 604/164 X |

*Primary Examiner*—Peter A. Aschenbrenner
*Attorney, Agent, or Firm*—Peter C. Richardson; Lawrence C. Akers; Aaron Passman

[57] ABSTRACT

An electrosurgical tubular trocar system has a hollow tube substantially longer than its diameter. The tube is shaped for insertion in a direction generally along its axis through tissue of a human or animal body. Distal and proximal ends on the tube enter and remain outside the tissue, respectively. A tip on the distal end punctures tissue of a human or animal. An insulating portion of high dielectric material extends along the tube between the distal and proximal ends. An electrode on the insulating portion extends from the proximal end to the tip to transmit radio frequency energy. An energy supply at the electrode proximal end permits the passage of energy to the tip. An electrosurgical generator as part of the energy supply has a control to regulate the amplitude and frequency of the energy. A return path in circuit with the tip and the energy supply cuts and/or coagulates. A tip point at an acute angle to the axis lessens the initial force necessary for entry of the tube. The return path is a conductor on the insulating portion for bipolar cutting across a gap. A passage is made through the tissue. The tube may be conductive. The insulating portion may extend along the tube and be tubular. The electrode may be part of the tube when the conductor is on the insulating portion or the conductor may be part of the tube and the electrode may be on the insulating portion. The tube may be tapered from a smaller diameter at the tip and be smooth. The tip is chamfer and circular. An alternate system may have the return path as a conductive pad in contact with the tissue as a monopolar circuit. The tube may be in fluid communication for flow. A method of placing a trocar aligns an axis normal to the skin, energizes a generator, cuts electrosurgically tissue, drives the tube through the tissue, and disconnects the generator.

20 Claims, 2 Drawing Sheets

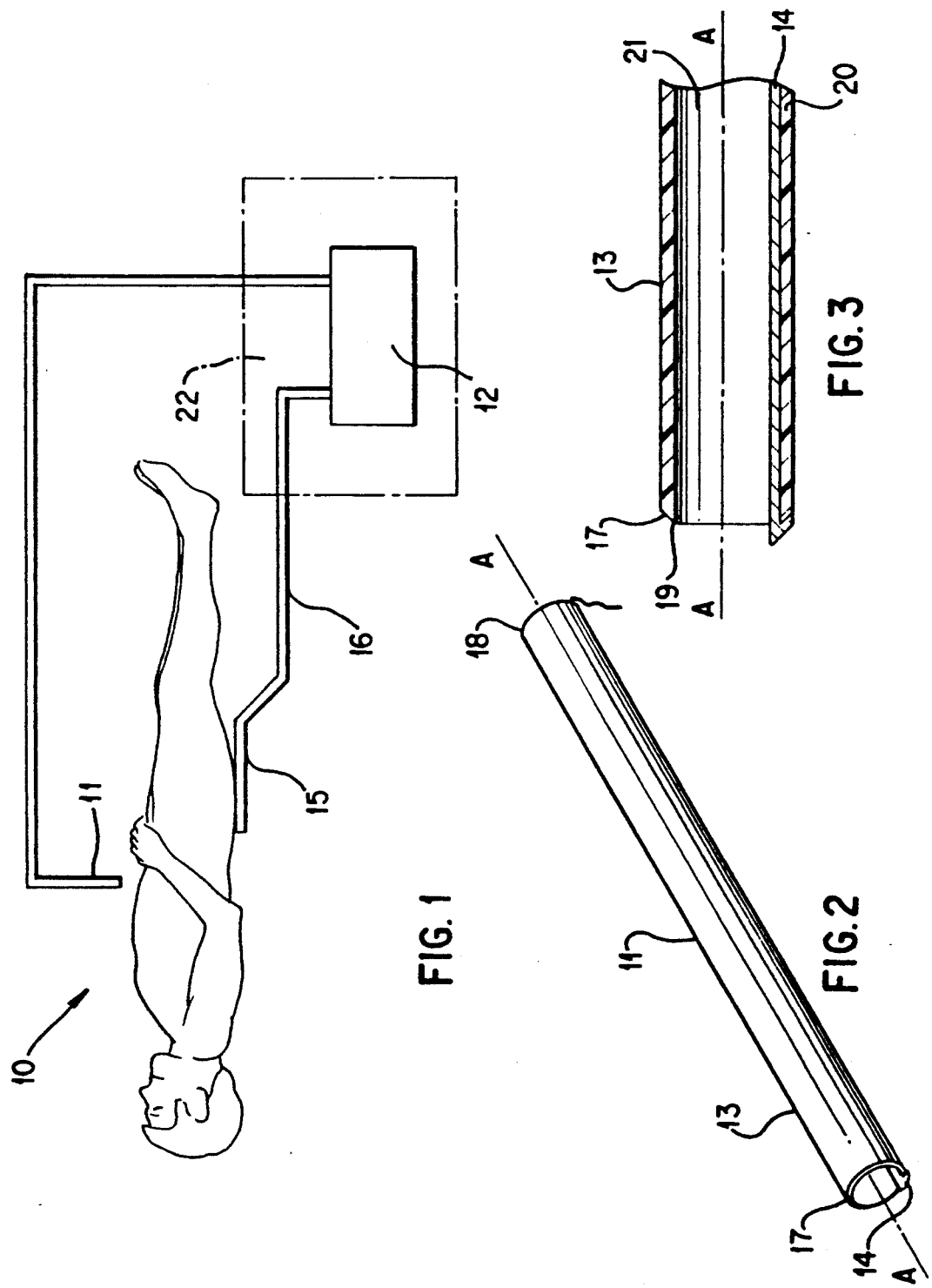

ELECTROSURGICAL TUBULAR TROCAR

FIELD OF THE INVENTION

An electrosurgical tubular trocar to cut tissue of a human or animal, and more specifically the electrosurgical tubular trocar for coring a tunnel through tissue and coagulating the tissue passage made thereby.

BACKGROUND OF THE DISCLOSURE

Surgery through a trocar inserted cannula and particularly with an opening through the tissue of an animal or human abdominal wall has become an important means to minimize the extent of surgical invasion. The lessening of invasion improves the cosmetic result, shortens recovery and lowers the cost. Endoscopic internal surgical procedures and equipment are available and in use for a variety of medical operations including gall bladder, bowel and gynecological surgery. A proper and simple instrument to open the passage through the abdominal wall and provide a passage for surgical instruments such as laparoscopes, endoscopes and the like is needed.

U.S. Pat. No. 3,595,239 discloses a catheter tube having an obturator in the form of an electrode passing coaxially therethrough. The obturator electrode is connected to an electrosurgical generator in order to provide high frequency energy used to divide or cut tissue thereby forming a passage for the catheter coaxially about the obturator to pass therewith through the tissue. The tip of the obturator extends beyond the catheter tip and cuts the path for the over the obturator catheter. The catheter moves along with the obturator electrode by means of a ring disposed about the obturator proximal to the tip and inside the tip of the catheter. There is no disclosure of an electrosurgical tubular cutting element for opening a passage.

A copending application incorporated by reference and made a part of this disclosure is U.S. Ser. No. 7-823093, assigned to a common owner. The disclosure in that application has a means for sensing the impedance or load associated with the energy required to do the cutting during insertion of an obturator tip so that the energy may be automatically ceased when the load has changed meaningfully. That approach is useful with the electrosurgical tubular trocar disclosed herein because safe use of it may be augmented by the combination of the circuitry described therein with the trocar explained in this disclosure.

U.S. Pat. No. 4,232,676 has a knife blade which cuts and cauterizes the incision and in so doing self limits the current flow at the knife. Specifically, the flat scalpel like blade carries electrodes therewith. Across the electrodes current flows when there is a conductive path. After cutting the current cauterizes the incision sealing the wound and eliminating the current path. The cutting and coagulation are electrosurgical. A flat ceramic insulator supports the electrodes between which radio frequency current flows. The configuration and method for cutting and coagulation electrosurgically is bipolar so no teaching of monopolar cutting and coagulation exists. A monopolar tool and the dangers of changing loads realized upon reaching the inner cavity of the body remain unappreciated in the disclosure of U.S. Pat. No. 4,232,676.

U.S. Pat. Nos. 4,601,710 and 4,654,030 are incorporated herein by reference and made a part hereof. Those patents explain laparoscopic procedures with obturators in trocar tubes shielded by a sleeve. The obturators include sharpened tips that first pierce the tissue and carry the trocar coaxially thereabout into the body. The shielding sleeve may project beyond the sharpened tip thereby covering and guarding it after entry into the body cavity. Various automatic mechanical mechanisms are disclosed that activate the shield after penetration. No electrosurgical cutting is taught to lower the effort required of the surgeon to penetrate the body wall. Considerable physical force and subsequent control are needed to effectively place the trocar through the abdominal wall without accidentally puncturing the bowel or other internal organs. The shielding provided in recognition of the almost impossible dexterity required to make a proper penetration has not eliminated the excessive force needed to drive the sharpened tip inward. Trocars are typically between 5 and 10 millimeters in diameter and the unit loading, kilograms per square millimeter, although reduced by the sharpened tip is significant.

U.S. Pat. No. 4,535,773 discloses techniques for shielding the sharp tip of a trocar by either interposing an extensible shielding sleeve or retracting the trocar into its tube. With regard to the latter, a solenoid operated detent holds the trocar in an extended position relative its tube and electronic sensing in the tip of the trocar is used to activate the detent for release. Nothing in this reference has any disclosure of electrosurgical cutting with a tubular trocar with an impedance responsive circuit to regulate an electrosurgical generator, attached to an electrosurgical cutting tip. The sensors and switches are disclosed in conjunction with a probe which retracts during penetration. In particular, the probe extends beyond the cutting surface until the abdominal wall has been traversed. The sensors can be connected to an audible or visual signal to indicate completion of the puncture. The switches could be mechanical or magnetic, be tripped by a sleeve in the puncturing instrument, a probe or a spring wire protruding from the tip or blade of a sharp pointed cutter. Multiple sensors in the cutting probe and the cannula can be used to signal the penetration position.

U.S. Pat. No. 4,919,653 discloses a device for locating epidural space. The release of force on the tip of a needle triggers an alarm which activate a solenoid latch permitting the needle and its sleeve to move in a cannula in response to an activated electromagnet such that the distal end moves 2 mm into the epidural space. Pressure sensors detect when the depression or release of pressure occurs as the needle enters the epidural space. The pressure signal is converted to produce the voltage difference between the sensor and the potentiometer. This difference is shown on a meter. The pressure sensor can be a small membrane with electrical contacts which are closed in the unloaded position and open when the membrane moves when the epidural space is reached. The passage of current through the contacts keeps the circuit open by means of a relay.

To safely place a cannula by a trocar technique requires knowledge of the position of the distal cutting tip thereof. The cutting edge, tip, is used to open the passage for the cannula through the animal or human tissue of the abdominal wall. A device to eliminate the needed to instantly indicate when the cutting tip has passed through the tissue and reached the inside of the body is needed so that the internal organs are not injured. Because the organs fill the inside cavity and are close to the wall there is the possibility of injury before the surgeon can stop advancing the distal cutting tip. A lessening of the forced needed to penetrate will improve control and reduce the likelihood of accidental injury. This is particularly so wherein the control of the energy applied to the electrosurgery is regulated according to load.

SUMMARY OF THE DISCLOSURE

A electrosurgical tubular trocar system may have a hollow tube elongate relative to an axis thereof and being substantially longer than its diameter. The tube is preferably shaped for insertion in a direction generally along the axis through tissue of a human or animal body in a puncture procedure. A distal end and a proximal end on the tube so the distal end may enter the tissue and the proximal end may remain outside the tissue. A tip on the distal end of the tube is in position for puncture through the tissue of a human or animal. An insulating portion of high dielectric material extends along the tube from the distal end to the proximal end.

An electrode associated with the insulating portion and extending from the proximal end to the tip may transmit radio frequency energy from the proximal end to the tip.

An energy supply associated with the electrode at the proximal end most preferably permits the passage of radio frequency energy between the proximal end and the tip. An electrosurgical generator as part of the energy supply may provide radio frequency energy. The electrosurgical generator may have a control to regulate the amplitude and frequency of the energy. A return path between the tip and the energy supply for completing the circuit thereby provides electrosurgical cutting and/or coagulation during the puncture procedure through tissue of a human or animal body.

The tip is most preferably beveled to a point at an acute angle to the axis to lessen the initial force necessary for entry of the circular cross sectional shape of the tube into the tissue of a human or animal. The return path between the tip and the energy supply for completing the circuit may preferably be a conductor on the insulating portion extending from the distal end to the proximal end for providing bipolar cutting at the distal end. A gap between the conductor and the electrode at the distal end provides bipolar cutting. The electrosurgical generator control regulates the radio frequency of the energy to coagulate tissue near the conductor and the electrode for forms a passage through the tissue. The tube may be a conductive material.

The insulating portion of high dielectric material may extend along the tube from the distal end to the proximal end and be tubular in shape. The electrode may be a part of the tube and the conductor is preferably on the tubular insulating portion for bipolar electrosurgery at the tip. The conductor may be a part of the tube and the electrode may be on the tubular insulating portion for bipolar electrosurgery at the tip. The tube is preferably tapered from a smaller diameter at the distal end to a larger diameter at the proximal end if it is desired to be able to ease the insertion through the tissue. The tube may preferably have a smooth surface finish to minimize the frictional forces between the tissue and the tube during penetration. The tip may have a chamfer to reduce the initial force necessary to enter the tissue. It is preferred that the tube is generally circular in cross section and has a diameter in the range of 5 to 10 millimeters.

An alternate system may have the return path provided by a conductive pad in contact with the tissue of the human or animal. The conductive pad and the electrode may form a monopolar electrosurgical circuit across which current flows from the tip through the tissue. The tube may preferably be connected in fluid communication to a source of fluid flow for moving material through the tube either toward the tip or away from the tip.

A method of placing an electrosurgical tubular trocar through the abdominal wall of a human or animal may include steps. Aligning an axis of an elongate tube having an electrode and a return path for radio frequency energy generally normal to the outside abdominal surface skin of the human or animal may preferably be the first step. Energizing an electrosurgical generator connected across the electrode and the return path at a proximal end of the tube may follow the first step. Cutting electrosurgically tissue near a distal end of the tube during application of penetration force to the tube along the axis may thereafter be performed. Driving the tube through the tissue of the abdominal wall while monitoring energy required for electrosurgical cutting until a measurable energy decrease occurs may then be accomplished by the surgeon. Disconnecting the electrosurgical generator from either the electrode or return path when the energy decreases may prevent injury to internal organs that are not intended to be cut. The method of placing an electrosurgical tubular trocar may have before the step of driving the added step of a cut down procedure used surgically to open the skin of the abdomen to facilitate the healing of the opening. The step of driving may begin with the step of entering the cut down tissue with a sharpened beveled tip thereby lessening the force initially needed to penetrate the subdermal tissue of the abdominal wall of a human or animal.

BRIEF DESCRIPTION OF THE DRAWINGS

FIG. 1 is a schematic illustration of the preferred embodiment of an electrosurgical trocar system showing the relationship of human or animal to the circuit used to provide energy to ease penetration of the abdominal wall.

FIG. 2 is a perspective view of the electrosurgical trocar of the preferred embodiment of the tube used to form a passage through the abdominal wall and specifically a monopolar configuration as shown in FIG. 1.

FIG. 3 is an enlarged illustration in cross section of the distal end of the trocar as seen along line 3—3 of FIG. 2 and including the electrode passing along the inside of the tube thereof.

DETAILED DESCRIPTION OF THE DRAWINGS

Figure 4:
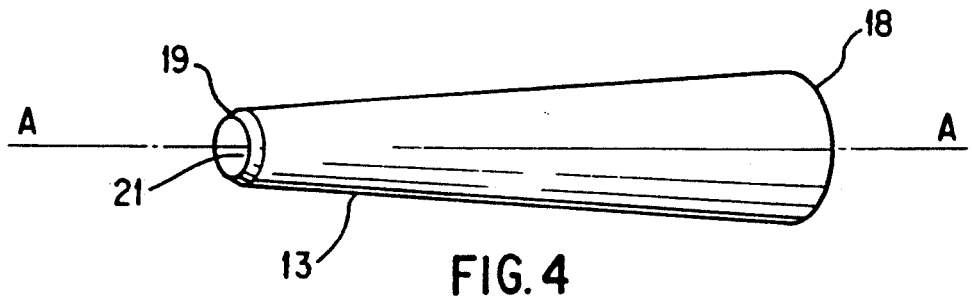
FIG. 4 is an alternate electrosurgical configuration shown in perspective wherein the tube is tapered from a smaller diameter at the distal end to a larger diameter at the proximal end and with a chamfer about the tip.

An electrosurgical tubular trocar system 10 is shown in FIG. 1 as a monopolar configuration in a schematic representation applied to an abdominal wall of a human. An electrosurgical tubular trocar 11 is shown connected to an electrosurgical generator 12 such as, a Valleylab Force 2 unit, made at 5920 Longbow Drive, Boulder, Colo. 80301. The electrosurgical tubular trocar 11 in FIG. 2, a perspective view of a preferred embodiment, includes a hollow tube 13 elongate relative to a central axis "A" thereof and the hollow tube 13 is substantially longer than it is wide across its diameter. Identical reference numbering is used throughout the various FIGS. 1 to 7 herein for referring to the same components of the different embodiments in order to aid in the understanding of the disclosure. The hollow tube 13 of FIGS. 1 and 2 are monopolar in that an electrode 14 is on the hollow tube 13 and a grounding pad 15 as a return path 16 for the electrosurgical radio frequency energy supplied by the electrosurgical generator 12 completes the circuit as illustrated in FIG. 1.

In FIG. 2 there is a distal end 17 and a proximal end 18 on the hollow tube 11. The distal end 17 is used to make entry into the tissue of the human or animal and most preferably through the abdominal wall while the proximal end 18 remains outside the tissue. The electrosurgical tubular trocar 11 hollow tube 13 has a tip 19 on the distal end 17. The tip 19 is located and shaped for assisting puncture through the tissue of the abdominal wall.

The hollow tube 13 can be made of a number of materials such as high strength plastic, ceramic, or metal. If the tube 13 is made of metal, an insulating portion 20 of a high dielectric material must extend along the tube 13 from the distal end 17 to the proximal end 18. The insulating portion 20 can be a part of the tube 13 or can be laminated to the tube 13 or arranged in any fashion which will allow the tube 13 to retain a relatively thin wall and carry the monopolar electrode 14. The preferred tube 13 is somewhere between 3 to 10 millimeters in diameter and is used to make a passage 21 through the abdominal wall for endoscopic or laparoscopic procedures associated with surgery inside the body cavity thereinside. The electrode 14 is associated with the insulting portion 20 and extends from the proximal end 18 of the tube 13 to the tip 19 thereof. The electrode 14 is of a conductive material which permits the transmission of radio frequency energy along the hollow tube 13 from the proximal end 18 to the tip 19 so that the electrosurgical generator 12 may be connected to the electrode 14 outside of the body tissue whereby radio frequency energy can be transmitted to t he body tissue from the tip 19 of the hollow tube 13. Specifically, the size and shape of the electrode 14 is such that the energy transmitted therethrough may contract or connect with the tissue adjacent the tip 19 and complete the circuit to the return path 16 by means of the pad 15 shown in FIG. 1.

The electrosurgical generator 12 when connected in circuit with the electrode 14 near the proximal end 18 of the hollow tube 13 permits radio frequency energy to pass along the electrode 14 which is in the preferred monopolar embodiment and the hollow tube 13 is thus shown as an insulator. Radio frequency energy at the tip 19 provides electrosurgical cutting of tissue thereagainst for reducing the force needed at the tip 19 of the hollow tube 13 to enter and penetrate the abdominal wall during an insertion procedure. Complete penetration provides the passage 21 in the form of the hollow tube 13 which can later be removed or left in place in accord with the particular desire of the surgeon and the design of the hollow tube 13. That is to say that the tube 13 can be made of a size and construction which will permit it to remain in place during a laparoscopic or endoscopic procedure. The electrode 14 can be arranged so that it can be removed from the tube 13, if desired, after the tube 13 has penetrated through the abdominal wall.

The preferred hollow tube 13 of FIGS. 1 and 2 is an insulator of a high dielectric and the electrode 14, which is metal, preferably extends along the inside of the hollow tube 13. FIG. 3 is an enlarged side partial cross-sectional view as would be seen along line 3—3 of FIG. 2. It is apparent that the electrode 14 hooks over the tip 19 and those skilled in the art should appreciate that the electrode 14 could be, after the hollow tube 13 has been placed by advancement through the abdominal wall, similarly advanced relative to the tube 13 such that the electrode 14 can be separated from the tube 13 by unhooking the electrode 14 where it wraps around the tube 13 tip 19 as shown in FIG. 3. The electrode 14 once advanced can be rotated so that the unhooked electrode 14 may be drawn up through the center of the hollow tube 13 along the length of the axis "A" thereof and withdrawn completely from the placed tube, which can then act as the passage 21 for laparoscopic or endoscopic devices. Alternatively the hollow tube 13 can be removed and replaced with a cannula (not shown) or left in place with the electrode 14 as shown in FIG. 3. Simply disconnecting the electrode 14 from the generator 12 should be sufficient particularly wherein the thickness of the electrode 14 is such that the inside diameter of the hollow tube 13 is not obstructed.

The electrosurgical generator 12 as shown on the monopolar arrangement of FIG. 1 is part of an energy supply 22 that has the usual controls for providing radio frequency energy to regulate amplitude and frequency of energy delivered to the electrode 14 such that the electrode 14 can be used for cutting and/or coagulation. The cutting would preferably be subsequent to a slight cut down procedure used to open the surface tissue in a manner that can be easily closed and in a way whereby the resulting scarring is minimized. Once the exterior tissue has been cut down, the hollow tube 13 and electrode 14 combination which constitutes the electrosurgical tubular trocar 11 can be placed into the cut down and radio frequency energy passed between the electrode 14 and the return path 16 such as the pad 15 shown in FIG. 1 to cause electrosurgical cutting and/or cautery as the hollow tube 13 is inserted through the abdominal wall. The electrosurgery reduces the amount of force necessary to drive the hollow electrosurgical tubular trocar 11 in through the abdominal wall to the abdominal cavity. The hollow tube 13 can be designed to receive at its proximal end 18 insufflation plumbing including a valve and a $CO^2$ supply whereby the placed hollow tube 13 will have functioned initially as a means by which the abdominal cavity can be entered and thereafter inflated. The same hollow tube 13 can, as explained, then provide the passage 21 for laparoscopic or endoscopic procedures.

FIG. 4 illustrates an alternative shape for the hollow tube 13 with a taper from its distal end 17 to its proximal end 18. The tip 19 can be chamfered, i.e. having a greater angle relative to the axis "A" of the tube 13 whereby initial penetration and complete insertion are simplified in that the force required is less since the tube 13 diameter is smaller at the distal end 17 than it is at the proximal end 18.

Figure 5:
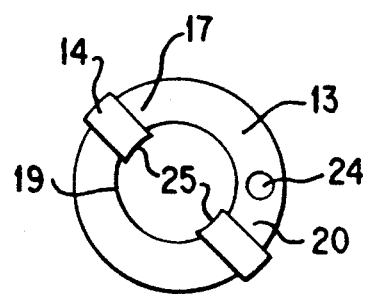
FIG. 5 is an enlarged view of the distal end of an alternative electrosurgical trocar wherein the electrode configuration is bipolar at the tip a channel is provided for a viewing optic fiber.
Figure 6:
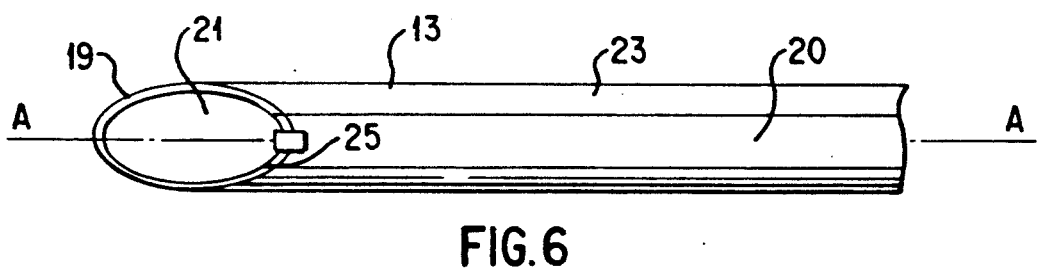
FIG. 6 is a top plan view of an electrosurgical trocar with a beveled tip at the distal end and showing an insulating portion associated with the tube.
Figure 7:
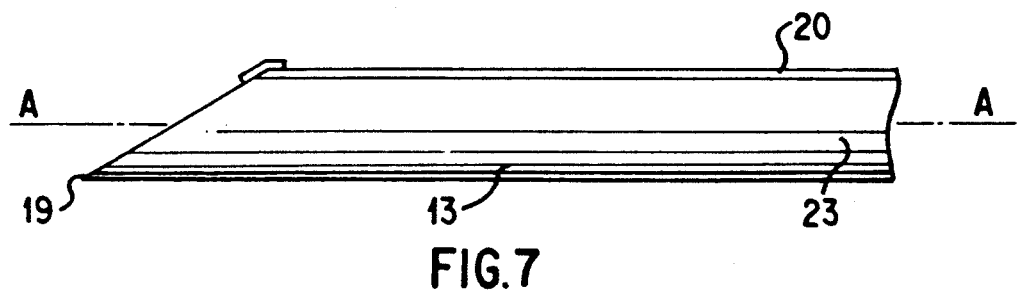
FIG. 7 is a side elevational view of the electrosurgical trocar of FIG. 6 wherein the acute angle of the bevel at the tip is shown and the electrode is where it wraps outwardly from the inside is depicted.

The return path 16 for the electrosurgical energy from the electrode 14 at the tip 19 need not be monopolar or specifically the pad 15 in FIG. 1 shown placed next to the patient. The return path 16 can, alternatively, be bipolar such as shown in FIG. 5, an enlarged view of the distal end 17 of an alternate electrosurgical tubular trocar 11, or as would be possible in another electrosurgical tubular trocar 11 design with a beveled tip 19 and integral insulating portion 20 as depicted in FIG. 6. If the hollow tube 13 was a metal conductor 23 such as medical grade stainless steel and the electrode 14 was carried on the integral insulating portion 20 extending therealong, electrosurgical energy could flow from the electrode 14 to the hollow tube 13 in a manner which would form a bipolar configuration. Such a configuration would not require a separate return path 16 in the form of pad 15.

In FIG. 5, electrodes 14 and conductor 23 are shown on the distal end 17 of tube 13 which preferably would be of a high dielectric material such as ceramic or plastic and that tube 13 also has a longitudinal circular channel 24, to include, for example, an optical catheter, used to view the procedure before, during, and/or after the penetration of the abdominal wall. It will be noted also that the tip 19 in FIGS. 6 and 7 includes the beveled tip 19 such as applied, for example to a hypodermic needle, that beveled tip 19 is used to aid in the insertion of the tube 13. The beveled tip 19 is at an angle which is acute relative to the axis "A" of the hollow tube 13 and is arranged so as to minimize the trauma resulting from the insertion and the effort required to make the penetration. Even with the beveled tip 19 cut down is preferred to reduce scarring.

As shown in FIGS. 5 and 6 there is a gap 25 between the electrode 14 and the conductor 23 provided for the return path 16. This gap 25 is arranged so that an arc forms thereacross between the electrode 14 and the conductor 23 at the tip 19 of the hollow tube 13, thus providing electrosurgical cutting. The surgical generator 12 can be adjusted to provide a radio frequency compatible for coagulating tissue and/or cutting tissue as required during the procedure of entry, through for example, the abdominal wall of a human or animal. As an alternate, the circuit for electrosurgery can be through the metal tube 13 and the return path 16 through conductor 23 which could be on the insulating portion 20 thereby forming a bipolar configuration. It is preferred that the tube 13 be of materials, whether a metal, an insulator, or a combination, that have a smooth outer surface finish to minimize the frictional forces between the electrosurgical tubular trocar 11 and the tissue through which it is inserted during the penetration procedure. Trauma would, thereby be minimizing the forces required to make the insertion reduced.

While a circular tube 13 is shown and a preferred diameter would be in the range of 5-10 millimeters, those dimensions and configurations are not required, they are only preferred in view of the laparoscopic and endoscopic procedures currently possible. It is expected that other shapes and sizes may be appropriate so as to minimize the effect of the intrusion procedures which exist or are developed in the future. In addition to the insertion procedure, it might be appropriate to connect the proximal end 18 of the tube 13 to a source of fluid flow for moving material that finds its way into the hollow tube 13, as a consequence of the electrosurgical cutting through the body of the human or animal when the electrosurgical tubular trocar 11 is passed.

A method for inserting the electrosurgical tubular trocar 11 through the abdominal wall of a human or animal may include several steps. Aligning the axis "A" of the elongate hollow tube 13 carrying the electrode 14 normal to the outside of the abdominal surface skin of a human or animal begins the method and is shown schematically in FIG. 1. The electrosurgical generator 12 is used to energize the electrode 14 and cause current to flow therefrom to the return path 16, so that a circuit of electrosurgical energy will pass from the tip 19 of the tube 13 through the tissue of the human or animal and aid in cutting electrosurgically near the tip 19 during application of penetrating force to the tube 13. The penetrating force is applied along the axis "A" of the tube 13 at the proximal end 18 so as to drive the tube 13 through the tissue of the abdominal wall while the energy consumed during the process is monitored until a measurable decrease in energy occurs at which time the electrosurgical generator 12 is disconnected from the electrode 14 or the return path 16 in order to prevent further electrosurgical cutting once the abdominal wall has been opened and the passage 21 has been made into the abdominal body cavity. The method of placing the trocar electrosurgically can also include a cut down procedure first made in the abdominal wall exterior tissue prior to opening the passage 21 electrosurgically. The cut down is to facilitate the healing of the opening and this step of entering the cut down with the tube 13 can be facilitated by having the sharpened or beveled tip 19 on the electrosurgical tubular trocar 11 thereby lessening the force initially needed to penetrate the subdermal tissue of the abdominal wall.

It is preferred that the electrode 14 material be conductive for radio frequency energy and any suitable material which will conduct radio frequency energy would be appropriate. If the tube 13 is metal, any medical grade metal such as stainless steel, would function appropriately. This is not to say that other materials could not be used or that other combinations of materials, insulators, and conductors or could not be arranged in combination. So long as they provide a monopolar or bipolar radio frequency circuit relative to an electrosurgical tubular trocar 11, they would fall within the scope of the claims of the present invention.

What is claimed is:

1. An electrosurgical tubular trocar system comprising a hollow tube elongate relative to an axis thereof and being substantially longer than its diameter, the tube shaped for insertion in a direction generally along the axis through tissue of a human or animal body in a puncture procedure;

a distal end and a proximal end on the tube, the distal end for entering the tissue and the proximal end for remaining outside the tissue;

a tip on the distal end of the tube in position for puncture through the tissue of a human or animal;

an insulating portion of high dielectric material extending along the tube from the distal end to the proximal end;

an electrode associated with the insulating portion and extending from the proximal end to the tip for transmitting radio frequency energy from the proximal end to the tip;

an energy supply associated with the electrode at the proximal end for permitting the passage of radio frequency energy between the proximal end and the tip;

an electrosurgical generator as part of the energy supply for providing radio frequency energy, the electrosurgical generator including a control to regulate the amplitude and frequency of the energy, and a return path between the tip and the energy supply for completing the circuit thereby providing electrosurgical cutting and/or coagulation during the puncture procedure through tissue of a human or animal body.

2. The electrosurgical tubular trocar system of claim 1 wherein the tip is beveled to a point at an acute angle to the axis to lessen the initial force necessary for entry of the circular cross sectional shape of the tube into the tissue of a human or animal.

3. The electrosurgical tubular trocar system of claim 1 wherein the return path between the tip and the energy supply for completing the circuit is a conductor on the insulating portion extending from the distal end to the proximal end for providing bipolar cutting at the distal end.

4. The electrosurgical tubular trocar system of claim 3 wherein a gap between the conductor and the electrode at the distal end provides bipolar cutting.

5. The electrosurgical tubular trocar system of claim 3 wherein the electrosurgical generator control regulates the radio frequency of the energy to coagulate tissue near the conductor and the electrode for forming a passage through the tissue.

6. The electrosurgical tubular trocar system of claim 1 wherein the tube is a conductive material.

7. The electrosurgical tubular trocar system of claim 6 wherein the insulating portion of high dielectric material extending along the tube from the distal end to the proximal end is tubular in shape.

8. The electrosurgical tubular trocar system of claim 7 wherein the electrode is a part of the tube and the conductor is on the tubular insulating portion for bipolar electrosurgery at the tip.

9. The electrosurgical tubular trocar system of claim 7 wherein the conductor is a part of the tube and the electrode is on the tubular insulating portion for bipolar electrosurgery at the tip.

10. The electrosurgical tubular trocar system of claim 1 wherein the tube is tapered from a smaller diameter at the distal end to a larger diameter at the proximal end to ease the insertion through the tissue.

11. The electrosurgical tubular trocar system of claim 1 wherein the tube has a smooth surface finish to minimize the frictional forces between the tissue and the tube during penetration.

12. The electrosurgical tubular trocar system of claim 2 wherein the tip has a chamfer to reduce the initial force necessary to enter the tissue.

13. The electrosurgical tubular trocar system of claim 2 wherein the tube is generally circular in cross section and has a diameter in the range of 5 to 10 millimeters.

14. The electrosurgical tubular trocar system of claim 1 wherein the return path is provided by a conductive pad in contact with the tissue of the human or animal.

15. The electrosurgical tubular trocar system of claim 14 wherein the conductive pad and the electrode form a monopolar electrosurgical circuit across which current flows from the tip through the tissue.

16. The electrosurgical tubular trocar system of claim 1 wherein the tube is connected in fluid communication to a source of fluid flow for moving material through the tube either toward the tip or away from the tip.

17. An electrosurgical trocar system comprising:

a hollow tube elongate relative to an axis thereof and being substantially longer than its diameter, a circular cross section shape for the tube for insertion in a direction generally along the axis and normal to its diameter through tissue of a human or animal body in a puncture procedure, the tube having conductive material, the tube with a surface finish used to minimize the frictional forces between the tissue and the tube during penetration;

a distal end and a proximal end on the tube, the distal end for entering the tissue and the proximal end for remaining outside the tissue;

a tip on the distal end of the tube in position for puncture through the tissue of a human or animal, a bevel at an angle to the axis on the tip to aid in the entry of the circular cross sectional shape of the tube into the tissue of a human or animal;

an insulating portion of high dielectric material tubular in shape extends with the tube from the distal end to the proximal end;

an electrode associated with the insulating portion and extending from the proximal end to the tip for transmitting radio frequency energy from the proximal end to the tip, the electrode carried as a part of the tube;

an energy supply associated with the electrode at the proximal end for permitting the passage of radio frequency energy between the proximal end and the tip;

an electrosurgical generator as part of the energy supply for providing radio frequency energy, the electrosurgical generator including a control to regulate the amplitude and frequency of the energy, the electrosurgical generator control regulates the radio frequency of the energy;

a return path between the tip and the energy supply for completing the circuit thereby providing electrosurgical cutting and/or coagulation during the puncture procedure through tissue of a human or animal body to coagulate tissue between and the electrode along the elongate length of the tube for forming a passage through the tissue;

a conductor as part of the return path and on the insulating portion extends from the distal end to the proximal end for providing bipolar cutting, and a gap between the conductor and the electrode at the distal end across which bipolar cutting for bipolar electrosurgery near the tip.

18. A method of placing an electrosurgical tubular trocar through the abdominal wall of a human or animal including the following steps:

aligning an axis of an elongate tube having an electrode and a return path for radio frequency energy generally normal to the outside abdominal surface skin of the human or animal;

energizing an electrosurgical generator connected across the electrode and the return path at a proximal end of the tube;

cutting electrosurgically tissue near a distal end of the tube during application of penetration force to the tube along the axis;

driving the tube through the tissue of the abdominal wall while monitoring energy required for electrosurgical cutting until a measurable energy decrease occurs, and disconnecting the electrosurgical generator from either the electrode or return path when the energy decreases.

19. The method of placing an electrosurgical tubular trocar of claim 18 wherein before the step of driving begins a cut down procedure opens surgically the skin of the abdomen to facilitate the healing of the opening.

20. The method of placing an electrosurgical tubular trocar of claim 19 wherein the step of driving begins with entering the cut down tissue with a sharpened beveled tip thereby lessening the force initially needed to penetrate the subdermal tissue of the abdominal wall of a human or animal.

* * * * *